United States Patent [19]
Szamosi et al.

[11] Patent Number: 5,696,024
[45] Date of Patent: Dec. 9, 1997

[54] HERBICIDAL WATER SOLUBLE GRANULAR COMPOSITIONS

[75] Inventors: Janos Szamosi, Yardley, Pa.; Mimi Schaaf, Princeton, N.J.

[73] Assignee: American Cyanmid, Madison, N.J.

[21] Appl. No.: 466,654

[22] Filed: Jun. 6, 1995

[51] Int. Cl.⁶ .................... A01N 43/50; A01N 43/42
[52] U.S. Cl. ............... 504/139; 504/253; 71/DIG. 1
[58] Field of Search .................... 504/139, 253; 71/DIG. 1

[56] References Cited

U.S. PATENT DOCUMENTS

| | | | |
|---|---|---|---|
| 4,816,060 | 3/1989 | Steller et al. | 71/92 |
| 5,221,319 | 6/1993 | Van Haften et al. | 504/144 |
| 5,256,625 | 10/1993 | Bussler et al. | 504/107 |
| 5,266,553 | 11/1993 | Champion et al. | 504/206 |
| 5,280,008 | 1/1994 | Chaoy et al. | 504/116 |
| 5,294,596 | 3/1994 | Haas et al. | 504/225 |
| 5,328,889 | 7/1994 | Van Haften et al. | 504/116 |
| 5,334,576 | 8/1994 | Doehner, Jr. et al. | 504/128 |
| 5,461,019 | 10/1995 | Willms et al. | 504/130 |
| 5,488,027 | 1/1996 | Bauer et al. | 504/105 |

*Primary Examiner*—S. Mark Clardy
*Attorney, Agent, or Firm*—John W. Hogan, Jr.

[57] ABSTRACT

The present invention provides a solid water soluble granular composition which comprises an imidazolinone herbicide alone or in combination with a second herbicide and a base, preferably wherein the base is present at a ratio of about 0.9 to 2.0 molar equivalents of base to molar equivalents of imidazolinone herbicide. Said composition is storage stable and dissolves rapidly and essentially completely in water for even application to target surfaces.

9 Claims, No Drawings

HERBICIDAL WATER SOLUBLE GRANULAR COMPOSITIONS

BACKGROUND OF THE INVENTION

Increasingly, agricultural formulation research is turning to solid compositions for enhanced safe handling and beneficial environmental impact. Health and environmental concerns posed by solvent-based liquid concentrates, aqueous suspension concentrates and water dispersible powders or granules which are packaged in plastic or metal containers are continually being addressed.

Imidazolinone compounds are a class of highly potent, environmentally benign, crop selective herbicides which contain a pyridine or quinoline carboxylic acid functionality ortho to the imidazolinone ring. However, the imidazolinone ring is known to be unstable and subject to degradation in the presence of a base. Although solid, water soluble, herbicidal salt compositions of substituted phenoxy and benzoic acid compounds and methods of their preparation are known, none of said compounds are particularly susceptible to base degradation (U.S. Pat. No. 5,266,553 and U.S. Pat. No. 5,328,889).

Therefore, it is an object of this invention to provide a solid imidazolinone composition which is essentially completely water soluble and storage stable.

It is another object of this invention to provide an agricultural composition having environmentally desirable characteristics and safe and easy handling for farmers, operators and applicators.

These and further objects and features of the invention will become more evident in the detailed description set forth hereinbelow.

SUMMARY OF THE INVENTION

The present invention provides a solid, water soluble, herbicidal composition which comprises an imidazolinone herbicide alone or in combination with a second herbicide and a base, preferably wherein the base is present at a ratio of about 0.9 to 2.0 molar equivalents of base to molar equivalents of imidazolinone herbicide. Said composition is suitable for packaging in water soluble materials for an environmentally compatible and safe agricultural product which upon complete dissolution results in even application to all target surfaces.

DETAILED DESCRIPTION OF THE INVENTION

Imidazolinone pyridine and quinoline carboxylic acid herbicides are zwitterionic compounds which have relatively low water solubility. Solubility increases with increased pH as the carboxylic acid becomes ionized. However, at pH>7 the imidazolinone ring may be unstable. Therefore, in order to enhance storage stability and avoid product degradation, formulations of this very valuable agricultural product have been liquid compositions such as heterogeneous suspension concentrates or acidic aqueous concentrates which are frost-sensitive and require costly packaging materials, or solid compositions such as water dispersible granulars or wettable powders which may require cumbersome mechanical mixing procedures and which give a heterogeneous application product subject to settling, uneven application and potential clogging of spray apparatus.

It has now been found that a composition comprising an imidazolinone herbicide alone or in combination with a second herbicide and a base, preferably wherein the base is present at a ratio of about 0.9 to 2.0, more preferably about 1.1 to 1.7, molar equivalents of base to molar equivalents of imidazolinone herbicide is storage stable, frost-tolerant and essentially completely water soluble. The inventive composition is suitable for environmentally benign water soluble packaging, is safe and easy to handle and gives a homogeneous application product which ensures even application of the active ingredient to the target surface.

The imidazolinone herbicides may be one or more compounds of formula I

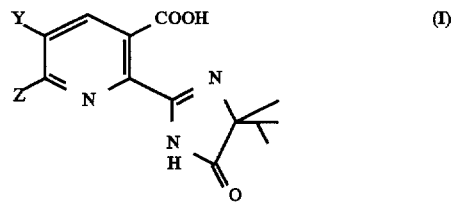

wherein Y and Z are each independently hydrogen, halogen, $C_1$–$C_4$ alkyl optionally substituted with halogen or $C_1$–$C_4$ alkoxy and Y and Z may be taken together to represent a structure —CH=CH—CH=CH—. Preferred imidazolinone herbicides are those of formula I wherein Z is hydrogen, Y is hydrogen, methyl, ethyl or methoxymethyl or when Y and Z are taken together to represent a structure —CH=CH—CH=CH—; for example, 2-(4-isopropyl-4-methyl-5-oxo-2-imidazolin-2-yl)nicotinic acid; 2-(4-isopropyl-4-methyl-5-oxo-2-imidazolin-2-yl)-5-methyl)nicotinic acid; 5-ethyl-2-(4-isopropyl-4-methyl-5-oxo-2-imidazolin-2-yl)nicotinic acid; 2-(4-isopropyl-4-methyl-5-oxo-2-imidazolin-2-yl)-3-quinolinecarboxylic acid or 2-(4-isopropyl-4-methyl-5-oxo-2-imidazolin-2-yl)-5-(methoxymethyl)nicotinic acid.

The base of the invention is any material which when added to a solution increases the pH. Among the bases suitable for use in the inventive composition are those most commonly known such as alkali metal hydroxides, i.e., NaOH, KOH and the like or alkali metal salts such as carbonates and bicarbonates, i.e., $Na_2CO_3$, $NaHCO_3$, $K_2CO_3$, $KHCO_3$ and the like, phosphates, i.e., $Na_3PO_4$, $K_3PO_4$ and so forth, preferably carbonates and bicarbonates. The amount of base may vary depending upon the water solubility of the imidazolinone herbicide employed as active ingredient. In general, the preferred amount of base is measured as a molar equivalent ratio to imidazolinone herbicide of about 0.9 to 2.0, more preferably about 1.1 to 1.17. Of course it is understood that a molar equivalent ratio greater than 2.0 will also yield a soluble composition, however excess base is generally undesirable.

Herbicides contemplated for use as the second herbicide in the composition of the invention are any water soluble herbicidally active compounds such as substituted phenoxy or benzoic acid salts such as (2,4-dichlorophenoxy)acetate salt (2,4-D), 4-(2,4-dichloro-phenoxy)butanoate salt (2,4-DB), 2-(4-chloro-2-methyl-phenoxy)propanoate salt (MCPP), 4-chloro-2(methylphen-oxy)acetate salt (MCPA), 2-(2,4-dichlorophenoxy)-propanoate salt (dichlorprop), 3,6-dichloro-2-methoxy-benzoate salt (dicamba), 3-amino-2,5-dichlorobenzoate salt (chloramben) and the like. The salt anion may be any standard carboxylic acid anion such as ammonium, organic ammonium, sodium, potassium and the like. The second herbicide may be present at 0% to 85% wt/wt.

The composition of the invention may also comprise standard formulation aides commonly used in a solid agricultural composition such as dyes, dispersing agents, inert fillers and the like. Dispersing agents such as alkyl naphthalene condensate, lignon sulfonate, polyethylene oxide, polypropylene oxide and the like, preferably alkyl naphthalene condensate, are suitable. Inert fillers which are water soluble such as sodium chloride, starch, sugar, and the like are preferred.

The composition of the invention may be prepared by standard dry compaction or extrusion techniques. In general, the dry ingredients are milled or blended mechanically and then either fed into a tablet press or a compactor, or the milled or blended powder is moistened, extruded and dried. The granular products are then sieved and screened using standard techniques to give dry granules of a uniform particle size.

In actual practice, all solid ingredients, including the imidazolinone herbicide and a base, preferably in a ratio of about 0.9 to 2.0, more preferably about 1.1 to 1.7, molar equivalents of imidazolinone to base are blended for about 30 minutes in a Munson mixer, manufactured by Munson Machinery Company, Utica, N.Y., or the equivalent thereof. Processing water about 7 to 12% wt/wt, preferably about 10% wt/wt, is sprayed into the blender while it is in operation and blending is continued for about 15 minutes. The resultant moistened blend is fed into a basket granulator and extruded. The extruded product is spread on trays and dried.

For a more clear understanding of the invention, specific examples are set forth below. These examples are merely illustrative and are not to be understood as limiting the scope and underlying principles of the invention in any way. Indeed, various modifications of the invention, in addition to those shown and described herein, will become apparent to those skilled in the art. Such modifications are also intended to fall within the scope of the appended claims.

EXAMPLE 1

Preparation of Herbicidal Water Soluble Granular Compositions

General Procedure

All solid ingredients are blended for about 30 minutes. Processing water, about 10% wt/wt, is sprayed onto the blended mixture while the blender is operating and blending is continued for about 15 minutes. The moistened blend is extruded using a standard LCI Corporation benchtop extruder (Charlotte, N.C.). The extrudate is dried on a fluid bed drier and the dried material is sieved to give a uniform particle size.

Using the above procedure, the following compositions shown in Table I are prepared and evaluated for storage stability.

All of the compositions in Table I are completely soluble in water at concentrations of 4 times the herbicide application rate (0.2 g granular composition/99.8 g water).

As can be seen from Table I all compositions are storage stable.

TABLE I

| Ingredient | Purpose | wt/wt % A | B | C |
|---|---|---|---|---|
| 2-(4-isopropyl-4-methyl-5-oxo-2-imidazolin-2-yl)-5-methoxymethyl) nicotinic acid (98.2% tech) | Imidazolinone Herbicide | 72.67 | 72.52 | 72.08 |
| Na$_2$CO$_3$ | Base | 11.55 | 2.90 | 19.22 |
| Aerosol OTB[1] | Dispersant | 0.61 | — | — |
| Igepon T77[2] | Dispersant | 0.61 | — | — |
| Morwet EFW[3] | Diapersant | — | 4.84 | 4.81 |
| STAR-DRI[4] | Inert Filler | 11.55 | 4.84 | — |
| NaCl | Inert Filler | — | 11.70 | — |
| Water | Residual Moisture | 3.00 | 3.20 | 3.90 |
| Ratio of Molar equivalents of Base to molar equivalents of herbicide | | 0.932 | 0.234 | 1.56 |
| Stability[5]-Initial (wt/wt % active ingredient) | | 71.05 | 71.05 | 72.8 |
| 3 months at 45° C. | | 69.75 | 70.05 | 72.6 |
| 1 month at 55° C. | | 71.20 | 72.85 | 73.5 |

[1]Cytech (Stamford, Connecticut)
[2]GAF Chemicals Corporation (Wayne, New Jersey)
[3]Witco (Houston, Texas)
[4]A.E. Staley Manufacturing Company (Decatur, Illinois)
[5]Margin of error of assay method is ±2%

EXAMPLE 2

Preparation of Herbicidal Water Soluble Granular Compositions Containing a Mixture of Active Ingredients Using essentially the same procedure described in Example I, except the dye is dissolved in the processing water, the following composition is prepared and evaluated.

| Ingredient | Purpose | wt/wt % |
|---|---|---|
| 5-Ethyl-2-(4-isopropyl-4-methyi-5-oxo-2-imidazolin-2-yl)nicotinic acid (96% tech.) | Imidazoiinone Herbicide | 19.92 |
| Sodium dicamba (78% tech.) | Second Herbicide | 73.56 |
| Sodium Carbonate | Base | 4.00 |
| Morwet EFW[1] | Dispersant | 1.00 |
| FD&C Blue[2] No. 1 | Dye | 0.01 |
| Sodium Chloride | Inert Filler | 1.51 |
| Ratio of Molar equivalents of Base to molar equivalents of imidazolinone herbicide | | 1.14 |

[1]Witco (Houston, Texas)
[2]Tricon Colors (Elmwood Park, New Jersey)

The test composition (2.0 g) is added to 98 g of water in a graduated cylinder. The cylinder is stoppered and inverted until a complete clear solution is obtained by visual observation. The test composition is soluble after 9–13 inversions.

EXAMPLE 3

Preparation of Herbicidal Water Soluble Granular Compositions

General Procedure

All dry ingredients are milled, then fed into a standard bench top tablet press and compressed at a pressure of about 500–1500 psi to give dry granules.

Using the above procedure, the following compositons are prepared and shown in Table II. All of the test compositions in Table II are soluble in water at concentrations of greater than 4 times the herbicide application rate.

TABLE II

Herbicidal Water Soluble Granular Compositions

| Ingredient | Purpose | (wt/wt %) | | | | | | | |
|---|---|---|---|---|---|---|---|---|---|
| | | A | B | C | D | E | F | G | h |
| 2-(4-isoporpyl-4-methyl-5-oxo-2-imidazolin-2-yl)-nicotinic acid | Imidazolinone Herbicide | 75.51 | — | — | — | — | — | — | — |
| 2-(4-isopropyl-4-methyl-5-oxo-2-imidazolin-2-yl)-5-methylnicotinic acid | Imidazolinone Herbicide | — | 77.96 | — | — | — | — | — | — |
| 5-ethyl-2-(4-isopropyl-4-methyl-5-oxo-2-imidazolin-2-yl)nicotinic acid | Imidazolinone Herbicide | — | — | 70.59 | 71.01 | 69.09 | — | — | — |
| 2-(4-isopropyl-4-methyl-5-oxo-2-imidazolin-2-yl)-3-quinolinecarboxylic acid | Imidazolinone Herbicide | — | — | — | — | — | 72.53 | 67.29 | 66.45 |
| $K_3PO_4$ | Base | 22.45 | 20.01 | 25.49 | — | — | 23.52 | — | — |
| $Na_2CO_3$ | Base | — | — | — | 28.40 | — | — | 32.07 | — |
| $NaHCO_3$ | Base | — | — | — | — | 30.30 | — | — | 32.89 |
| Aerosol OTB[1] | Dispersant | 0.20 | 2.02 | 0.65 | 0.60 | 0.60 | 0.22 | 0.63 | 0.66 |
| Morwet D-425[2] | Dispersant | — | — | 1.31 | — | — | — | — | — |
| Cellulose gum STAR-DRI[3] | Inert Filler | 0.82 | — | — | — | — | 1.76 | — | — |
| MYVAPLEX ® 600[4] | Inert filler | 1.02 | — | — | — | — | 1.96 | — | — |
| Ratio Molar equivalents of base to molar equivalents of imidazolinone herbicide | | 1.1 | 1.0 | 1.5 | 2.2 | 1.5 | 1.4 | 2.8 | 1.8 |

[1]Cytech (Stamford, Connecticut)
[2]Witco (Houston, Texas)
[3]A.E. Staley Manufacturing Company (Decatur, Illinois
[4]Eastman Chemical Company (Kingsport, Tennessee)

What is claimed is:

1. A herbicidal, water soluble, solid granular composition which comprises an imidazolinone herbicide and a water soluble base and optionally a second herbicide, said imidazolinone herbicide having the structure of formula I

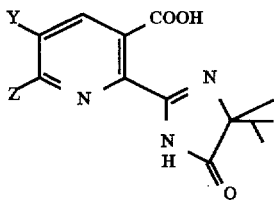

(I)

wherein Y and Z are each independently hydrogen, halogen, $C_1$–$C_4$ alkyl optionally substituted with halogen or $C_1$–$C_4$ alkoxy or Y and Z may be taken together to represent a structure —CH═CH—CH═CH—.

2. The composition according to claim 1 wherein the base is present at a ratio of about 0.9 to 2.0 molar equivalents of base to molar equivalents of imidazolinone herbicide.

3. The composition according to claim 1 wherein the second herbicide is a solid substituted benzoic acid salt or solid substituted phenoxy carboxylic acid salt and is present at about 0%–85% wt/wt.

4. The composition according to claim 1 wherein the base is an alkali metal hydroxide, an alkali metal carbonate or an alkaline earth metal phosphate.

5. The composition according to claim 2 having a formula I herbicide wherein Z is hydrogen; Y is hydrogen, methyl, ethyl or methoxymethyl; or Y and Z may be taken together to represent —CH═CH—CH═CH—.

6. The composition according to claim 1 wherein the second herbicide is the sodium salt of dicamba.

7. The composition according to claim 5 wherein the base is present at a ratio of about 1.1 to 1.8 molar equivalents of base to molar equivalents of imidazolinone herbicide.

8. The composition according to claim 6 wherein the imidazolinone herbicide is 5-ethyl-2-(4-isopropyl-4-methyl-5-oxo-2-imidazolin-2-yl)nicotinic acid.

9. The composition according to claim 8 wherein the base is sodium carbonate.

* * * * *